(12) United States Patent
Thorwarth et al.

(10) Patent No.: US 10,166,105 B2
(45) Date of Patent: Jan. 1, 2019

(54) SELF-DETACHING LAYER FOR EASY IMPLANT REMOVAL

(71) Applicant: DePuy Synthes Products, Inc., Raynham, MA (US)

(72) Inventors: Goetz Thorwarth, Langendorf (CH); Cyril Voisard, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/243,548

(22) Filed: Aug. 22, 2016

(65) Prior Publication Data

US 2016/0354208 A1  Dec. 8, 2016

Related U.S. Application Data

(63) Continuation of application No. 13/177,179, filed on Jul. 6, 2011.

(Continued)

(51) Int. Cl.
*A61F 2/28* (2006.01)
*A61F 2/30* (2006.01)
(Continued)

(52) U.S. Cl.
CPC .......... *A61F 2/30767* (2013.01); *A61B 17/72* (2013.01); *A61B 17/80* (2013.01); *A61B 17/842* (2013.01); *A61F 2/3094* (2013.01); *A61L 27/306* (2013.01); *A61L 27/32* (2013.01); *A61L 27/34* (2013.01); *A61L 27/58* (2013.01); *A61B 17/848* (2013.01); *A61B 2017/00004* (2013.01); *A61F 2002/2817* (2013.01); *A61F 2002/30064* (2013.01); *A61F 2002/30067* (2013.01); *A61F 2002/3093* (2013.01); *A61F 2002/3098* (2013.01); *A61F 2002/30672* (2013.01); *A61F 2002/30929* (2013.01); *A61F 2002/30932* (2013.01); *A61F 2002/30971* (2013.01); *A61F 2002/30981* (2013.01); *A61F 2210/0004* (2013.01); *A61F 2310/00023* (2013.01); *A61F 2310/00796* (2013.01);

(Continued)

(58) Field of Classification Search
CPC ........ A61F 2/30767; A61F 2002/30929; A61F 2002/30064; A61F 2002/2817; A61B 2017/0004; A61L 2420/02
See application file for complete search history.

(56) References Cited

U.S. PATENT DOCUMENTS 6,214,049 B1  4/2001 Gayer et al.
6,277,150 B1  8/2001 Crawley et al.
(Continued)

FOREIGN PATENT DOCUMENTS

CN  101411899  4/2009
CN  101505736  8/2009
(Continued)

*Primary Examiner* — Brian Dukert
(74) *Attorney, Agent, or Firm* — Fay Kaplun & Marcin, LLP

(57) ABSTRACT

A bone implant includes (a) a first layer provided over a first outer surface of the bone implant and being formed of a first material which is one of water-soluble and degradable in body fluids, the first layer having a first thickness and (b) a second layer provided over an outer periphery of the first layer and being formed of a biocompatible material, the second layer having a second thickness smaller than the first thickness.

16 Claims, 1 Drawing Sheet

Related U.S. Application Data

(60) Provisional application No. 61/362,923, filed on Jul. 9, 2010.

(51) Int. Cl.

| | |
|---|---|
| *A61B 17/72* | (2006.01) |
| *A61B 17/80* | (2006.01) |
| *A61B 17/84* | (2006.01) |
| *A61L 27/30* | (2006.01) |
| *A61L 27/34* | (2006.01) |
| *A61L 27/58* | (2006.01) |
| *A61L 27/32* | (2006.01) |
| *A61B 17/00* | (2006.01) |

(52) U.S. Cl.
CPC . *A61F 2310/00976* (2013.01); *A61L 2400/18* (2013.01); *A61L 2420/02* (2013.01); *A61L 2420/08* (2013.01); *A61L 2430/02* (2013.01)

(56) References Cited

U.S. PATENT DOCUMENTS

| | | |
|---|---|---|
| 2004/0115241 A1 | 6/2004 | Calhoun et al. |
| 2007/0016307 A1 | 1/2007 | Zimmermann et al. |
| 2008/0208313 A1 | 8/2008 | Yu et al. |
| 2009/0186068 A1 | 7/2009 | Miller et al. |

FOREIGN PATENT DOCUMENTS

| | | |
|---|---|---|
| DE | 10 2006 044415 | 3/2008 |
| EP | 0 523 926 | 1/1993 |
| EP | 1572258 | 9/2005 |
| JP | 2009/500087 | 1/2009 |
| WO | 03/068286 | 8/2003 |
| WO | 2004/047880 | 6/2004 |
| WO | 2006/116374 | 11/2006 |
| WO | 2007/006043 | 1/2007 |
| WO | 2008/005509 | 1/2008 |
| WO | 2009/048645 | 4/2009 |
| WO | 2009/091384 | 7/2009 |

SELF-DETACHING LAYER FOR EASY IMPLANT REMOVAL

PRIORITY CLAIM

The present application is a Continuation Application of U.S. patent application Ser. No. 13/177,179 filed on Jul. 6, 2011; which claims priority to U.S. Provisional Patent Application Ser. No. 61/362,923 filed on Jul. 9, 2010. The entire disclosures of these applications/patents are expressly incorporated herein by reference.

FIELD OF THE INVENTION

The present application generally relates to a device for removing a bone implant from a bone.

BACKGROUND OF THE INVENTION

In orthopedic surgery including the Trauma and Cranio-Maxillofacial field, it is often desirable to remove bone implant components after a desired level of healing. This may be due to cosmetic reasons and/or to allow for a complete regeneration around the implant site. With many state-of-the-art implants made of biocompatible alloys (e.g. Titanium-Aluminum-Niobium "Ti—Al—Nb"), surgeons are often confronted with implants that integrate too well into the surrounding tissue, making removal more invasive and damaging than necessary.

BRIEF SUMMARY OF THE INVENTION

The present invention relates to a system and method for coating a bone implant with soluble or biodegradable layers and biocompatible layers that prevent direct tissue contact with a tissue facing surface of the bone implant. An exemplary coating according to the present invention may be carried out by a variety of techniques, including dip or spray coating and physical or chemical vapor deposition (PVD/CVD). This results in a biocompatible "shield" formed directly over the tissue contacting surface providing favorable healing around the implant but which is more easily detached after a predefined time in vivo, liberating the implant from surrounding tissue and allowing for a less invasive and damaging removal process. An outer biocompatible layer formed over the first shield is subsequently resorbed on a longer timescale, its total volume and material properties being selected to render insignificant any adverse effect when implanted in vivo.

The present invention relates to an implant with a substrate material comprising a metal or metal alloy coated with a first layer having a thickness D comprising a material which is water-soluble or degradable in body fluids and a second layer having a thickness d<D placed over the first layer comprising a biocompatible material.

This implant provides a self-detaching coating on a metallic implant substrate, shielding the implant from bone ongrowth or ingrowth without hindering the healing process. This allows for an easy removal of the implant after it has fulfilled its temporary function in the body.

In an exemplary embodiment of the implant the second layer comprises a bioresorbable or bio-dissolving material.

In another embodiment of the implant the second layer comprises a non-resorbable or non-dissolving material In a further embodiment of the implant the second layer has a minimum thickness d of 1 nm, preferably of 10 nm. With a thickness of 10 nm the second layer acts as effective barrier to cell through—growth to reduce or block the relevant diffusion mechanism.

In a further embodiment of the implant the second layer has a maximum thickness d of 100 nm.

In again a further embodiment of the implant the second layer has a resorption/dissolution rate which is smaller than that of the first layer.

In still a further embodiment of the implant the time required for the resorption/dissolution of the second layer is in the range of 2 weeks to 3 months.

In another embodiment of the implant the first layer is made of a resorbable material. Preferred materials are polylactides (PLA) and Calciumphosphates (CaP). This configuration allows a cell through-growth which might lead to a weakened "cell-second layer-cell" structure that easily breaks upon removal of the bulk implant. After the first layer has dissolved/been resorbed, the second layer will be resorbed on a longer timescale.

In another embodiment of the implant the thickness D of the first layer is at least 10 µm, preferably at least 100 µm.

In yet another embodiment of the implant the thickness D of the first layer is at most 1000 µm, preferably at most 500 µm.

In still another embodiment of the implant the ratio of D/d is in the range of 10,000:1 and 1,000:1.

In a further embodiment of the implant the first layer comprises polyvinyl alcohol (PVA) or a polylactide.

In another embodiment of the implant the second layer comprises a non-resorbable metal, preferably titanium or a titanium alloy and has a thickness d of maximum 100 nm.

In another embodiment of the implant the second layer comprises hydroxyapatite and has a thickness d of maximum 10 µm.

In again another embodiment of the implant a third layer comprising a mixture of the materials of the first and second layers is interposed between the first layer and the second layer.

In yet another embodiment of the implant a further layer is applied on the second layer and on this further layer another layer comprising a biocompatible material is applied. The further layer comprises a material which is water-soluble or degradable in body fluids.

In a further embodiment of the implant the number of alternating layers comprising a material which is water-soluble or degradable in body fluids and a biocompatible material is 2 x, wherein x is 3 or larger.

In a further embodiment of the implant the material of the first layer is different from the material of the second layer.

In accordance with another aspect, a method for manufacturing of the implant is provided which comprises the steps of applying a material which is water-soluble or degradable in body fluids to a substrate comprising a metal or metal alloy to form a first layer on the substrate and applying a biocompatible material on the first layer.

In another embodiment of the method a mixture of the materials used in steps A and B is applied to the first layer before performing step B.

In a further embodiment of the method the application of the layers is made by dip coating or spray coating.

BRIEF DESCRIPTION OF THE DRAWINGS

Several embodiments of the invention will be described in the following by way of example and with reference to the accompanying drawings in which.

DETAILED DESCRIPTION OF THE INVENTION

The present invention relates to a coated bone implant for the fixation of a fractured or otherwise damaged or weakened bone and a method of producing such a bone implant. Embodiments of the present invention may be used for orthopaedic fixation, cranio-maxillofacial fixation or for the fixation of any other bone in a living body requiring short or long-term implantation of a bone implant. A bone plate according to an exemplary embodiment of the invention is coated with one or more layers of materials selected to prevent the bone plate from becoming integrated with tissue surrounding the bone implant during short or long-term implantation in vivo. One or more of the layers of material in the exemplary bone plate may be formed of resorbable materials exhibiting desired characteristics (e.g., resorption rate, biocompatibility, etc.). It is noted that although embodiments of the present invention are described with particular layer thickness and configurations and described in regard to the fixation of specific bones, any other thickness or configurations may be employed in the fixation of any bone without deviating from the spirit and scope of the invention. Furthermore, although embodiments of the present invention depict the deposition of layers on only one surface of a bone implant, any or all surfaces of the bone implant may be coated with the exemplary layers without deviating from the spirit and scope of the invention.

Figure 1:
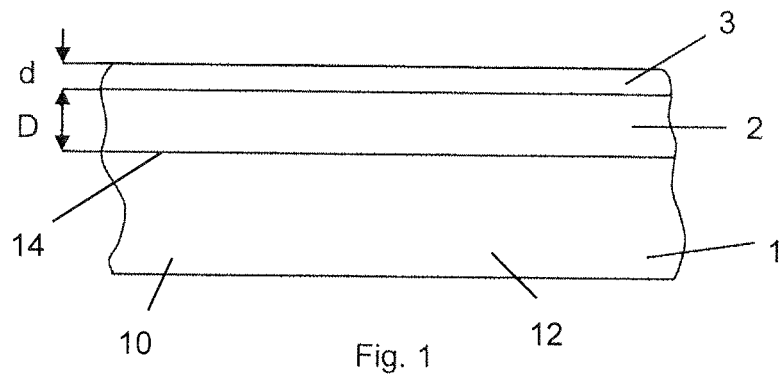
FIG. 1 illustrates a cross-section of a first exemplary embodiment of the implant according to the present invention.

As shown in FIG. 1, an implant 10 according to a first embodiment of the invention includes an implant body 12 (e.g., a bone plate or intramedullary nail) including a substrate material 1. A first surface 14 of the implant body 12 is coated with a first layer 2 with a second layer 3 extending over the first layer 2 so that the second layer 3 forms an outer surface of the implant 10 which, when implanted, forms a contact layer with the surrounding tissue. As would be understood by those skilled in the art, the substrate material 1 of the implant 10 may be any suitable metal, metal alloy, or polymer. Typically, for application as a surgical implant, the substrate material 1 is titanium (Ti), a Ti alloy such as $TiAl_6Nb_7$ ("TAN"), steel or PEEK, as those skilled in the art will understand.

The first layer 2 has a thickness D and includes a resorbable material comprising polyvinyl alcohol (PVA) or a polylactide. The thickness D of the first layer 2 can range from approximately 10 µm to 1000 µm, and in an exemplary embodiment may be between approximately 100 µm and 500 µm.

The second layer 3 has a thickness d and includes a biocompatible material which can be one of a bioresorbable or bio-dissolving material as well a non-resorbable or a non-dissolving material. In an exemplary embodiment, the second layer 3 comprises a non-resorbable metal, e.g. titanium or a titanium alloy and/or a hydroxyapatite. The thickness d of the second layer 3 is smaller than the thickness D of the first layer 2 and can range from 1 nm to 100 nm and, in a preferred embodiment, has a maximum thickness d of 10 µm. Further, the resorption/dissolution time for the second layer 3 is longer than that of the first layer 2 and ranges from 2 weeks to 3 months.

Due to the first layer 2 being formed on the surface 14 of the implant body 12 and the second layer 3 being formed on the first layer 2, contact between the tissue and the surface 14 of the implant body 12 is prevented. The biocompatible layer system formed by the first and second layers 2, 3 allows a favorable healing around the implant 10 as well as a less invasive and damaging procedure for removing the implant 10 due to the fact that at least the first layer 2 detaches from the implant body 12 after a predetermined time in vivo.

Figure 2:
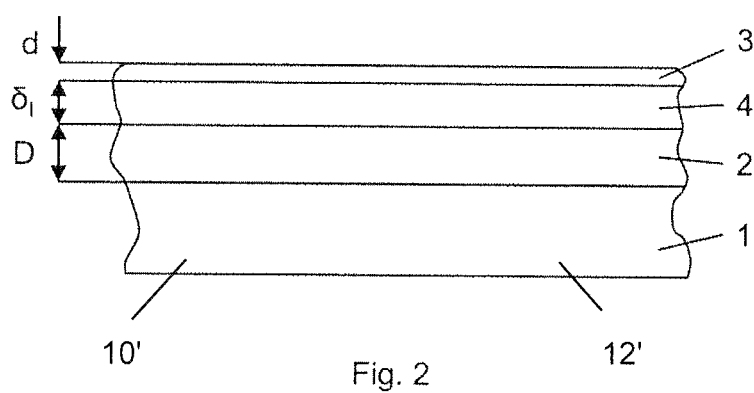
FIG. 2 illustrates a cross-section of another exemplary embodiment of the implant according to the present invention.

In FIG. 2, another embodiment of the implant is illustrated which differs from the embodiment of FIG. 1 only in that an intermediate layer 4 is formed between the first and second layers 2, 3 of an implant 10', The third layer 4 comprises a mixture of the materials of the first and second layer 2, 3. Similar to the embodiment of FIG. 1, an implant body 12' consisting of the substrate material 1 and having the form of a bone plate or an intramedullary nail is coated with the first layer 2 having a thickness D. The intermediate layer 4 is placed on the first layer 2 and has, for example, a thickness $\delta_I$ smaller than the thickness D of the first layer 2 and larger than the thickness d of the second layer 3 forming the contact layer with surrounding tissue.

Figure 3:
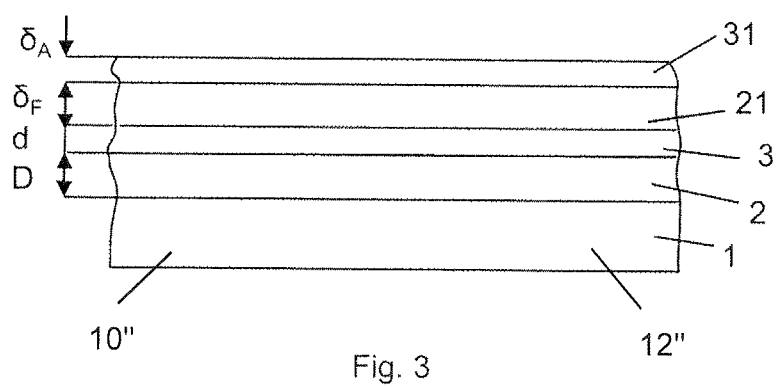
FIG. 3 illustrates a cross-section of a further exemplary embodiment of the implant according to the present invention.

Another embodiment of the implant is illustrated in FIG. 3 which differs from the embodiment of FIG. 1 only in that a third layer 21 is formed over the second layer 3. The third layer 21 includes a material that is water-soluble or degradable in body fluids. A fourth layer 31 formed over the third layer 21 includes a biocompatible material. Similarly to the embodiment of FIG. 1, an implant 10" having an implant body 12" consisting of the substrate material 1 formed as a bone plate or intramedullary nail is coated with the first layer 2 having the thickness D and the second layer 3 having the thickness d is placed on the first layer 2. The third layer 21 is placed on the second layer 3 and has a thickness $\delta_F$ which may, for example, have a thickness equal to the thickness D of the first layer 2 while the fourth and outermost layer 31 has a thickness $\delta_A$ which may be, for example, equal to the thickness d of the second layer 3. The fourth layer 31 forms the contact layer with surrounding tissue.

In accordance with an exemplary method for depositing layers over an implant according to the present invention, a bone plate commonly used for fracture fixation in combination with bone screws is used, The typical duration of in-vivo use of such bone plates ranges from a few weeks to a few months, after which they are often removed. The bone plates are typically fabricated from a TAN alloy or steel, but also can be made from plastics like PEEK. However, it is noted that exemplary bone plates according to the present invention may also be implanted indefinitely if so desired without deviating from the spirit and scope of the present invention.

According to a first exemplary step, a TAN bone plate is first cleaned by immersion in a 50/50 percentage by volume mixture of ethanol and acetone and subsequently placed into an ultrasonic bath for approximately five minutes. After this step, the implant is cleaned in a dry $CO_2$ gas jet. The implant is then coated with a water-soluble first layer 2 of polyvinyl alcohol (PVA) by dip coating in a PVA/water solution with a removal speed of XX mm/s, resulting in a PVA layer XX micrometers strong after drying, wherein, as those skilled in the art will understand, the removal speed is directly related to the resulting PVA layer strength. In a first exemplary embodiment, the removal speed may be 1 mm/s, resulting in a PVA layer of approximately 50 micrometers. The bone plate is then inserted into a vacuum system applying a pressure smaller than 1e-4 mbar. A 10 nm titanium oxide film is then deposited over the PVA layer by, for example, reactive magnetron sputtering with a working pressure of 5e-3 mbar in a mixture of 90% Ar and 10% $O_2$. The resulting second layer 3 is biocompatible and delays the water dissolution of the previously deposited PVA layer. The coated bone implant 10 is then removed from the vacuum chamber and packed in dry air or a vacuum. The first PVA layer 2 will detach in vivo after approximately one month, thus freeing the bone implant for removal following the removal of bone screws therefrom.

It will be appreciated by those skilled in the art that various modifications and alterations of the invention can be made without departing from the broad scope of the appended claims. Some of these have been discussed above and others will be apparent to those skilled in the art. For example, the exemplary layering according to the present invention may also be carried out on Kirschner wires or intramedullary nails without deviating from the spirit and scope of the present invention. In accordance with an exemplary technique according to the present invention, the Kirchner wire may be coated in substantially the same manner as discussed above, with a dip coating followed by a thermal evaporation process. If an intramedullary nail is used, the nail may be spray coated with a 100 μm thick biodegradable layer. The biodegradable layer may then be coated with a hydroxyapatite layer. Upon dissolution of the biodegradable layer (i.e., after implantation in vivo for a predetermined period of time), sufficient space remains between the intramedullary nail and the hydroxyapatite layer to permit removal of the intramedullary nail while still preventing an ingrowth of weak tissue therearound.

Although the invention and its advantages have been described in detail, it should be understood that various changes, substitutions, and alterations can be made herein without departing from the spirit and scope of the invention as defined by the appended claims. For example, any of the biodegradable layers of the present invention may be replaced by a melting interlayer, which may, for example, dissolve into surrounding tissue after reaching a predetermined temperature in the body (e.g. resting body temperature). In yet another example, bone implants requiring only short-term implantation may be provided with lubrication to prevent or reduce tissue growth thereover. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

What is claimed is:

1. A bone implant, comprising:
   a first layer provided over a first outer surface of the bone implant and including a first material which is one of water-soluble and degradable in body fluids, the first layer having a first thickness;
   a second layer provided over an outer surface of the first layer and formed of a second, biocompatible material, the second layer having a second thickness smaller than the first thickness;
   a third layer provided over an outer surface of the second layer, the third layer being formed of a material which is one of water-soluble and degradable in body fluids; and
   a fourth layer provided over an outer surface of the third layer, the fourth layer being formed of a biocompatible material.

2. The implant according to claim 1, wherein the second layer includes a bioresorbable or biodissolving material.

3. The implant according to claim 1, wherein the second layer includes a non-resorbable or nondissolving material.

4. The implant according to claim 3, wherein the second thickness is between 1 nm and 100 nm.

5. The implant according to claim 1, wherein the third layer has a third thickness equal to the first thickness.

6. The implant according to claim 1, wherein the first thickness of the first layer is between approximately 10 im and 1000 im, the ratio of the first thickness to the second thickness being in the range of 10,000:1 and 1,000:1.

7. The implant according to claim 1, wherein the first layer is formed of one of polyvinyl alcohol (PVA) and a polylactide.

8. The implant according to claim 7, wherein the second layer is formed of a non-resorbable metal.

9. The implant according to claim 7, wherein the second layer is formed of hydroxyapatite and has a maximum second thickness of 10 im.

10. The implant according to claim 1, further comprising:
    an intermediary layer interposed between the first layer and the second layer, the intermediary layer being formed of a mixture of the materials of the first and second layers.

11. The implant according to claim 1, wherein a number of alternating layers comprising a material which is water-soluble or degradable in body fluids and a biocompatible material is 2 x; x being 3 or larger.

12. The implant according to claim 1, wherein the fourth layer forms an outer surface of the implant which, when implanted forms a contact layer with surrounding tissue.

13. The implant according to claim 1, wherein the fourth layer has a fourth thickness equal to the second thickness.

14. The implant according to claim 7, wherein the second layer is formed of titanium or a titanium alloy with a maximum second thickness of 100 nm.

15. A method for manufacturing a bone implant, comprising:
    applying a first layer of a first material over a first surface of the bone implant, the first material being one or both of water-soluble and degradable in body fluids;
    applying a second layer of a second material over an outer surface of the first layer, the second material being biocompatible,
    applying a third layer of a third material over an outer surface of the second layer, the third material being water-soluble and degradable in body fluid,
    applying a fourth layer of a fourth material over an outer surface of the third layer, the fourth material being biocompatible; and
    applying an intermediary layer over the first layer prior to applying the second layer, the intermediary layer being formed of a mixture of the first and second materials.

16. The method according to claim 15, wherein the first, second, third and fourth layers are applied by one of dip coating and spray coating.

* * * * *

UNITED STATES PATENT AND TRADEMARK OFFICE
CERTIFICATE OF CORRECTION

PATENT NO. : 10,166,105 B2  
APPLICATION NO. : 15/243548  
DATED : January 1, 2019  
INVENTOR(S) : Thorwarth et al.

Page 1 of 1

It is certified that error appears in the above-identified patent and that said Letters Patent is hereby corrected as shown below:

In the Claims

Claim 15, Column 6, Line 55:
"water-soluble and degradable in body fluid,"
Should read:
"water-soluble and degradable in body fluids,"

Signed and Sealed this
Twenty-first Day of April, 2020

Andrei Iancu
*Director of the United States Patent and Trademark Office*